(12) United States Patent
Yang

(10) Patent No.: US 7,701,569 B2
(45) Date of Patent: Apr. 20, 2010

(54) DARK FIELD LIGHTING TESTING DEVICE

(75) Inventor: Chih-Yi Yang, Taipei (TW)

(73) Assignee: Lumos Technology Co., Ltd., Taipei (TW)

( * ) Notice: Subject to any disclaimer, the term of this patent is extended or adjusted under 35 U.S.C. 154(b) by 336 days.

(21) Appl. No.: 11/829,993

(22) Filed: Jul. 30, 2007

(65) Prior Publication Data

US 2009/0034251 A1 Feb. 5, 2009

(51) Int. Cl.
*G01N 21/00* (2006.01)
(52) U.S. Cl. .................. 356/237.2; 356/30; 356/237.6; 362/227; 362/236
(58) Field of Classification Search .................. 356/30, 356/237.1–237.6; 362/227–236
See application file for complete search history.

(56) References Cited

U.S. PATENT DOCUMENTS 7,420,657 B2 * 9/2008 Sasian et al. .................. 356/30
7,468,786 B2 * 12/2008 Wagner et al. ................ 356/30

\* cited by examiner

*Primary Examiner*—Gregory J Toatley, Jr.
*Assistant Examiner*—Iyabo S Alli
(74) *Attorney, Agent, or Firm*—Chun-Ming Shih

(57) ABSTRACT

A dark field lighting testing device, for detecting a surface defect of an object having mirror surfaces, includes a cavity, the interior surface of which is made of a light-absorbing material; an opening arranged on a top of the cavity; a tape body arranged on the interior surface of the cavity; a plurality of lighting elements arranged on the tape body and electrically connected to each other; and a plate body arranged right above the opening of the cavity. During testing procedure, light emitted from each lighting element is incident upon the surface of the tested object, from which the diffusively reflected or refracted light forms an image on the surface of the plate body, thus a defect on the surface of the tested body and a position thereof being able to be detected.

6 Claims, 5 Drawing Sheets

DARK FIELD LIGHTING TESTING DEVICE

BACKGROUND OF THE INVENTION

1. Field of the Invention

The present invention generally relates to an optical device, in particular, to a testing device having a dark field photograph for detecting a surface defect of an object.

2. Description of Prior Art

At present, dark field lighting technology is comprehensively applied to the testing procedure of an element or an object having a structure of mirror surfaces, for example, to the defect detection of surfaces of jewel, gem, and semiconductor element, etc. Essentially, a dark field lighting technology is to apply a light source to generate a light incident directly upon an object to be tested, through the diffusively reflective or refractive characteristics thereof, the diffusively reflected or refracted light forming an image, from which a defect on the tested object may be detected.

As shown in FIG. 1, which is a dark field testing device commonly seen, and the device includes: a cavity 10, the interior surfaces of which are all made of light-absorbing materials; an opening 101 arranged on the top of the cavity 10; a plate body 20 arranged in corresponding to the opening 101; a lighting element 30 arranged at the bottom of the cavity 10; a plurality of light-guiding tubes 40 closely surrounding the lighting elements 30 to guide the light from a light source toward an object 50 to be tested; and, a platform 102, on which the tested object is placed, and by which the light emitted from the lighting element 30 is blocked, such that the light guided by the light-guiding tubes 40 are directly incident upon the object 50 to be tested, which has the characteristics of reflection or refraction to focus an image on the surface of the plate body 20, whereby the optical image may be judged to determine whether a defect exists on the surface of the tested object or not.

However, in the prior detecting device, in which light-guiding tubes 40 are served as light-guiding paths and light sources of the dark field lighting, the object 50 to be tested has to be placed directly on the platform 102 with an artificially turning or rotating way to make the light of the light-guiding tube 40 incident upon the object to be tested from every aspect. Not only the testing efficiency is deteriorated, but also it easily results too insufficient light source to focus into an image through reflection and refraction, by applying the light-guiding tubes 40 as light-guiding paths, thanks to an indirectly lighting manner, so during testing judgment, this kind of uncertainty will influence the testing accuracy and becomes a problem needed to be solved urgently by those who are skilled in this art.

SUMMARY OF THE INVENTION

The invention is to provide a dark field lighting testing device capable of adjusting incident angles of the light source of the dark field by arranging a plurality of tape bodies possessing of a plurality of lighting elements. During test, light emitted from the lighting elements is directly incident upon an object to be tested from different incident aspects. Then, the diffusively reflected and refracted light is further focused into an image at the outside of a cavity, for facilitating a quick test in detecting a defect on the surface of the object to be tested.

The invention is mainly to provide a dark field lighting testing device for detecting a surface defect of an object having mirror surfaces, and the device includes: a cavity, the interior surface of which is made of a light-absorbing material; an opening arranged on a top of the cavity; a tape body arranged on the interior surface of the cavity; a plurality of lighting elements arranged on tape body and electrically connected to each other; and, a plate body arranged right above the opening of the cavity. During testing procedure, light emitted from each lighting element is incident upon the surface of the tested object, from which diffusively reflected or refracted light forms an image on the surface of the plate body. Thus, a defect on the surface of the tested body and a position thereof can be detected.

BRIEF DESCRIPTION OF DRAWING

The features of the invention believed to be novel are set forth with particularity in the appended claims. The invention itself, however, may be best understood by reference to the following detailed description of the invention, which describes a number of exemplary embodiments of the invention, taken in conjunction with the accompanying drawings, in which:

DETAILED DESCRIPTION OF THE INVENTION

In cooperation with attached drawings, the technical contents and detailed description of the present invention are described thereinafter according to several preferable embodiments, being not used to limit its executing scope. Any equivalent variation and modification made according to appended claims is all covered by the claims claimed by the present invention.

Figure 1:
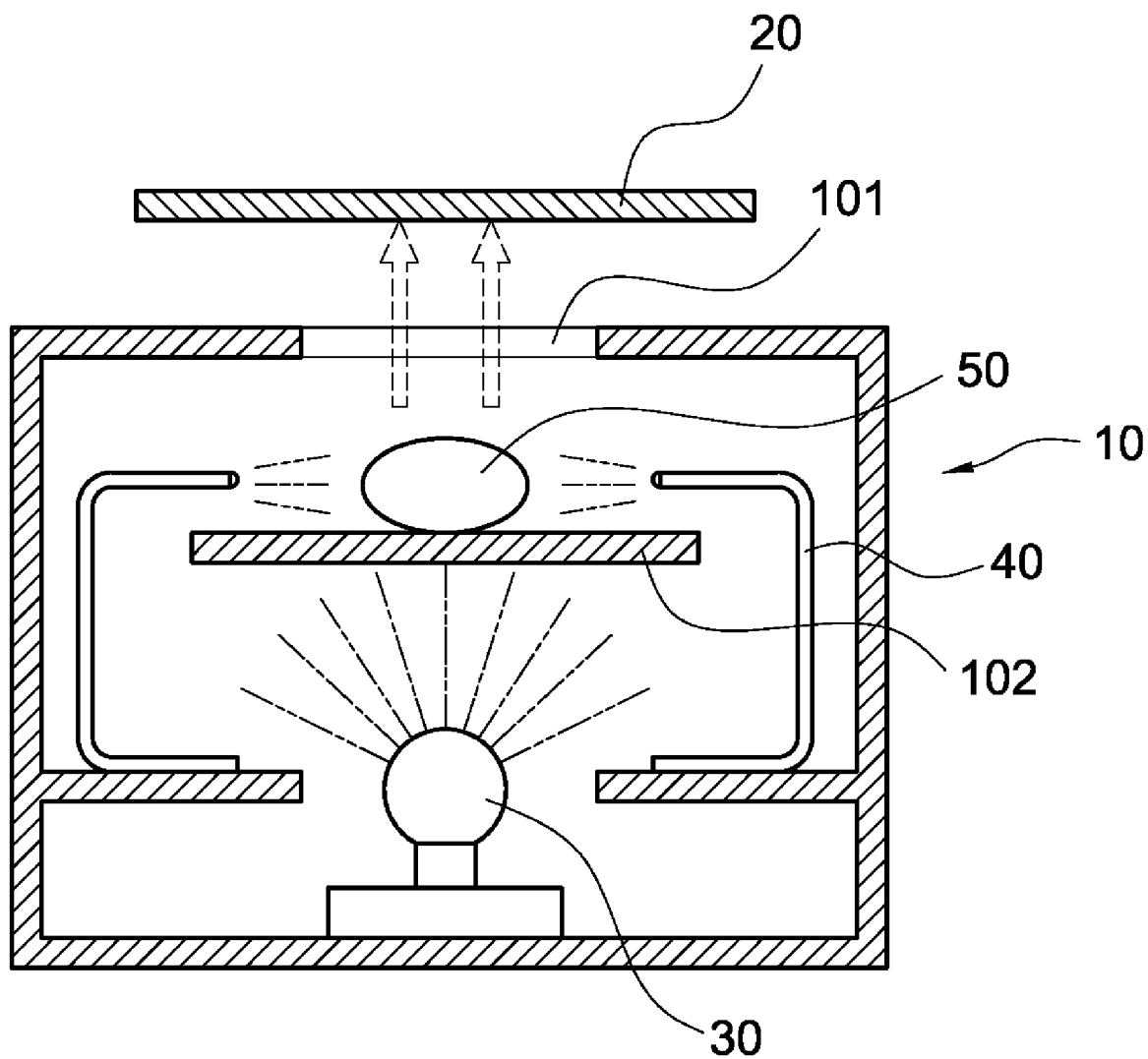
FIG. 1 is a structurally sectional view of the invention.
Figure 2:
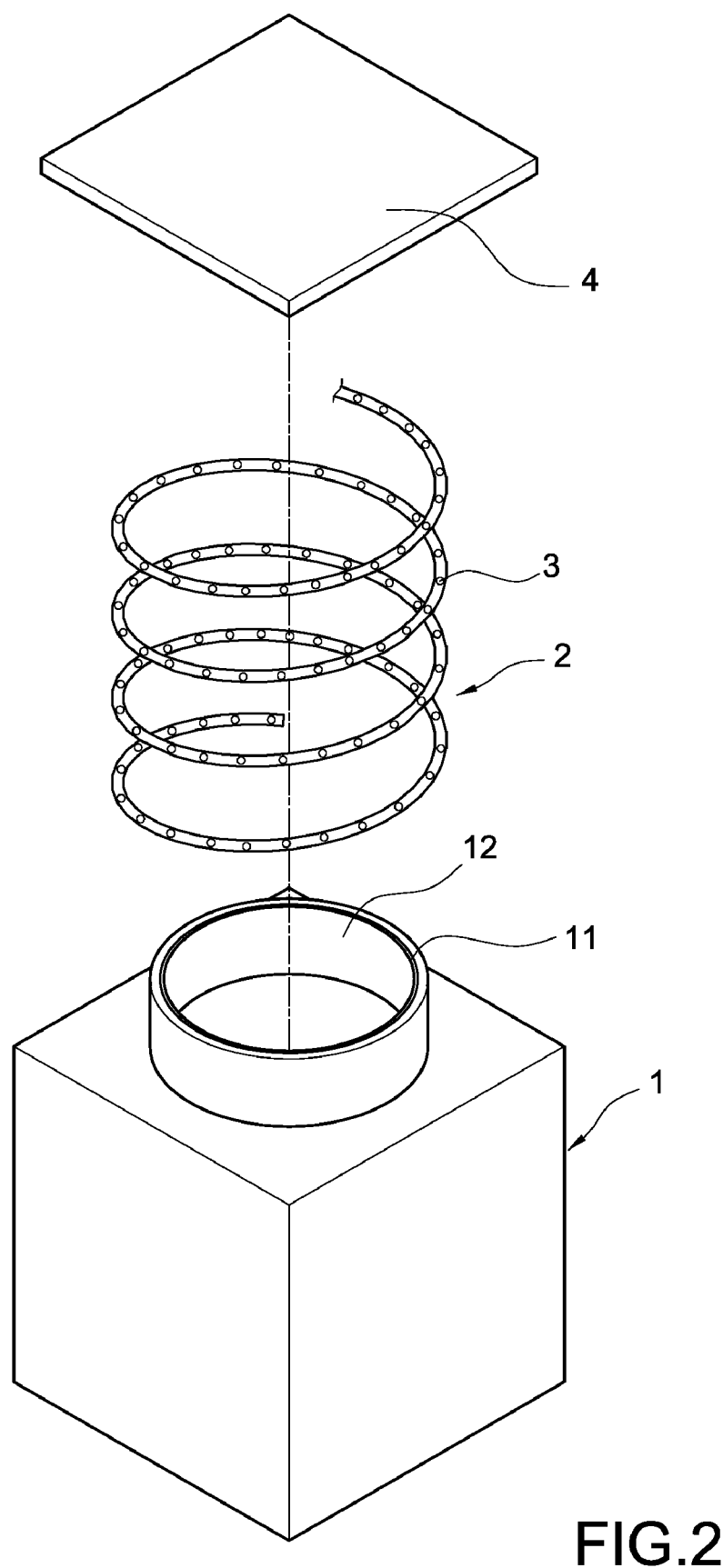
FIG. 2 is a structurally, explosively perspective view of the invention.
Figure 5:
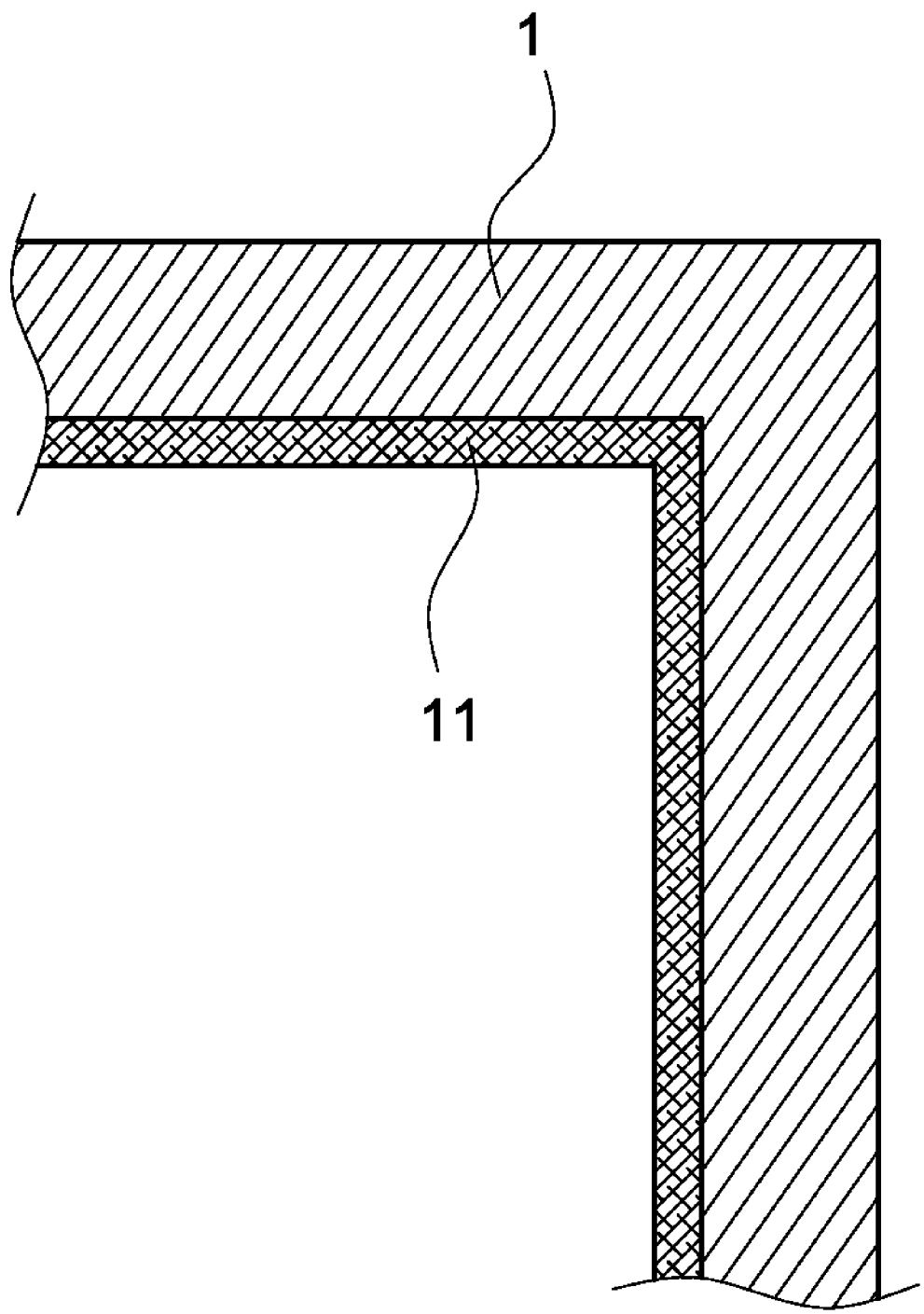
FIG. 5 is a locally enlarging illustration of a light-absorbing face according to another embodiment of the invention.

Please refer to FIG. 2, which is a structurally, explosively perspective view of the invention. As shown in this figure, the testing device of the invention includes: a cavity 1, the interior surface of which is a light-absorbing surface 11 and is constructed of black material, which is a black color in this embodiment or a black cloth as shown in FIG. 5; an opening 12, the position of which is right above the cavity 1 in this embodiment; a tape body 2 arranged over the light-absorbing surface 11 in the interior of the cavity 1; a plurality of lighting elements 3, each which is arranged on the tape body 2 and is an LED in this embodiment, and which are electrically connected to each other; a plate body 4 arranged right above the opening 12 of the cavity 1 for blocking the light reflected from the interior of the cavity 1, in the meantime, making the light reflected from the interior of the cavity focus an image thereon.

Figure 3:
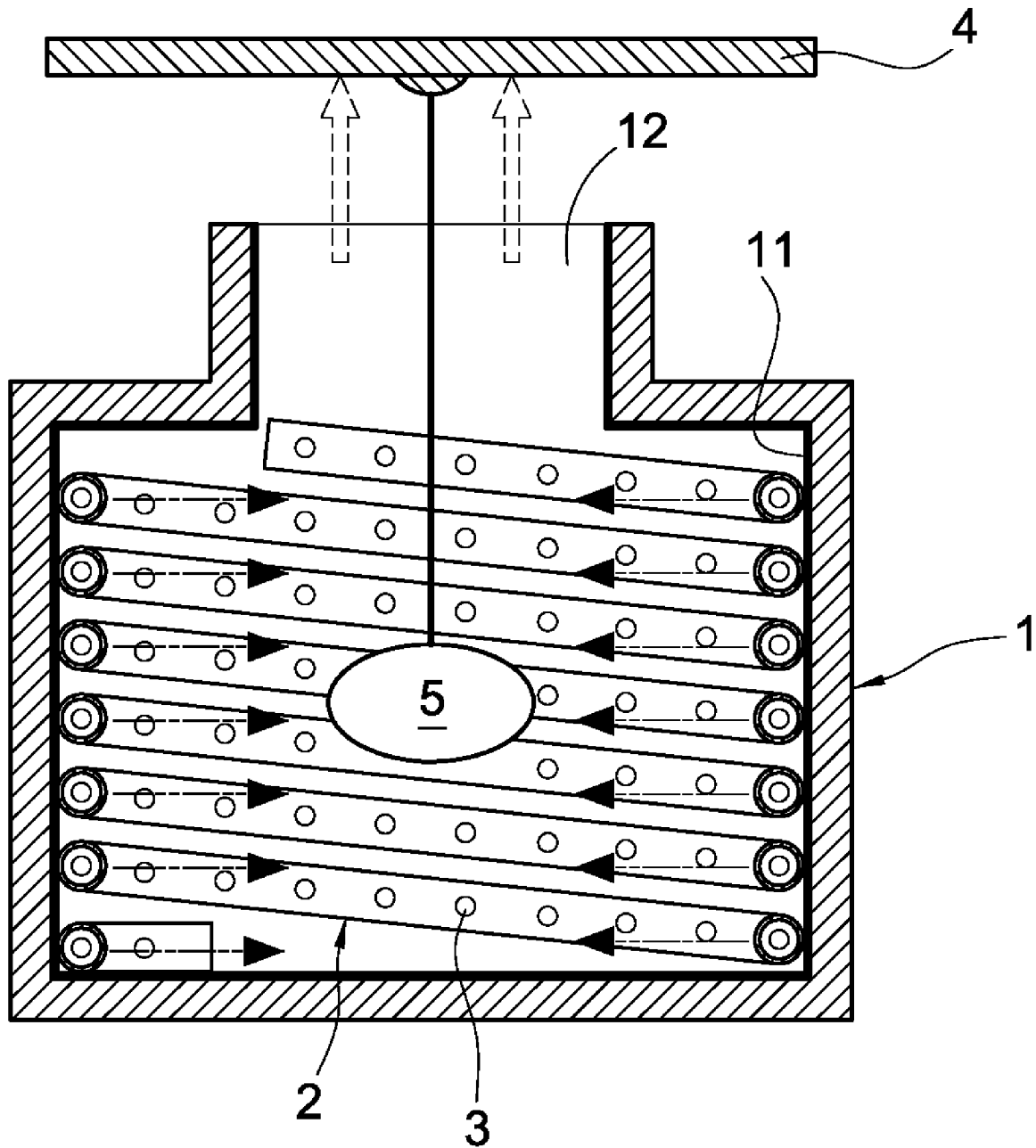
FIG. 3 is an operationally sectional illustration of the invention.

Please refer to FIG. 3, which is an operationally sectional view of the invention. As shown in this figure, the testing device according to the present invention is applied for the testing of an object 5 having mirror surface or curved surface. In addition, the object 5 to be tested has a diffusively reflecting or refracting function, for example, possessed by jewel or semiconductor element having mirror surface. During testing operation, the object 5 to be tested is hanged in the interior of the cavity 1. Then, power is supplied to the tape body 2 surrounding closely to the object 5 to be tested in a way, such that light, emitted from a plurality of lighting elements 3 arranged on the tape body 2, is directly incident upon the surface of the object 5 to be tested. Since of the possession of the characteristics of a light's reflection or refraction, the object 5 to be tested reflects or refracts the incident light diffusively, which is partially absorbed by the light-absorbing face 11, and the rest is focused onto the plate body 4 arranged on the opening 12 of the cavity to form a light image, according to which a defect on the surface of the object 5 to be tested may be detected if it do exist.

Figure 4:
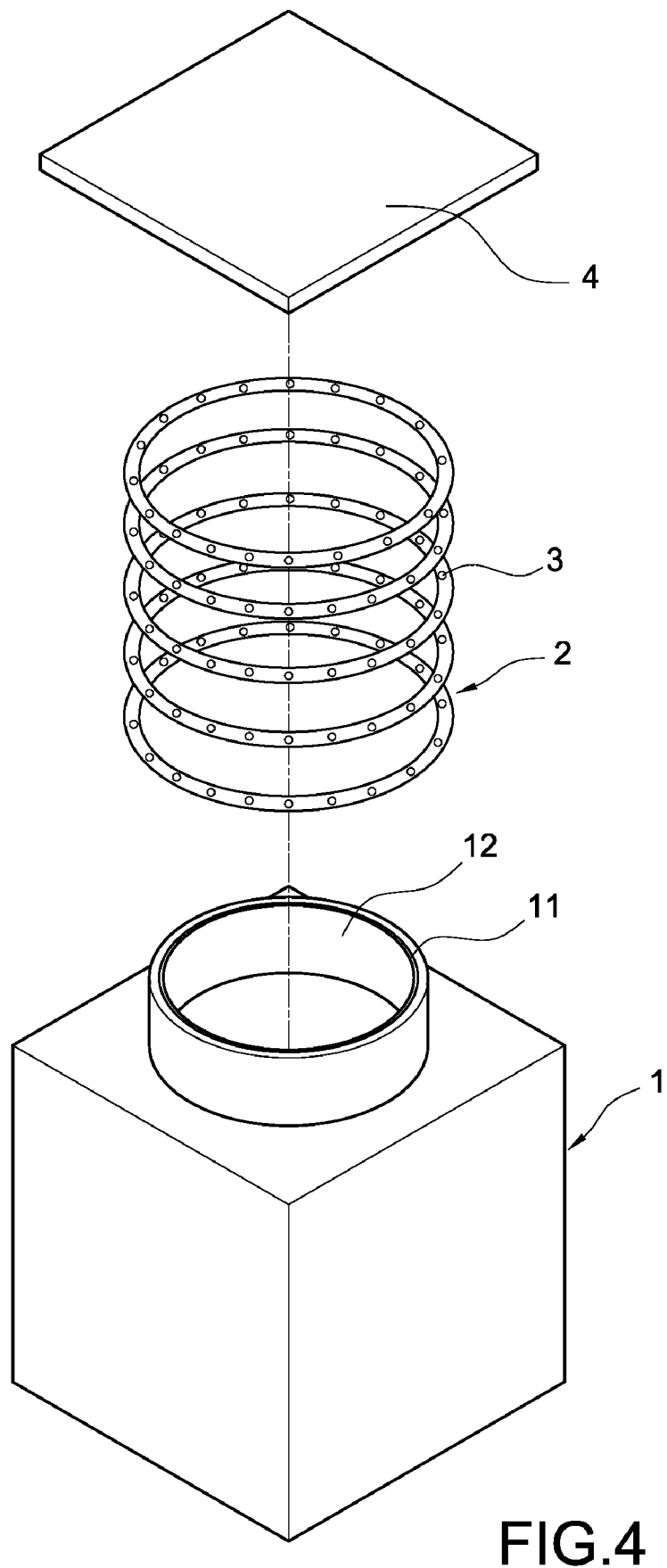
FIG. 4 is a perspective illustration according to another embodiment of the invention.

Please refer to FIG. 4, which a perspective illustration according to another embodiment of the present invention. In this case, except as a single tape body 2 arranged on the light-absorbing face 11 of the cavity 1 as described thereinbefore, the tape body 2 may also be designed as a ring-shaped configuration as shown in FIG. 4, which shows a plurality of ring-shaped tape bodies 2 interspaced on the light-absorbing face 11 of the cavity 1, and the lighting elements 3 arranged at a same tape body 2 are electrically connected to each other. By controlling the illumination of the lighting element 3 on different tape bodies 2, lights emitted from the light sources of different aspects are incident upon the mirrored faces of the object 5 to be tested, thereby a detection of defect on surface of the tested object 5 being able to achieve.

However, the aforementioned description is only a preferable embodiment according to the present invention, being not used to limit the patent scope of the invention, so equivalently structural variation made to the contents of the present invention, for example, description and drawings, is all covered by the claims claimed thereinafter.

What is claimed is:

1. A dark field lighting testing device, including:
   a cavity, an interior surface of which is a surrounding and light-absorbing surface, and on a top of which an opening is arranged;
   a tape body attached to an interior side surface of the cavity, the tape body being a helical-shaped tape or a ring-shaped tape;
   a plurality of lighting elements arranged on the tape body and electrically connected to each other; and
   a plate body spaced apart from the cavity, and arranged right above the opening of the cavity.

2. The dark field lighting testing device according to claim 1, wherein the lighting element is an LED.

3. The dark field lighting testing device according to claim 1, wherein the light-absorbing surface is constructed by a material with light-absorbing characteristic.

4. The dark field lighting testing device according to claim 3, wherein a color of the material is black.

5. The dark field lighting testing device according to claim 1, wherein the light-absorbing surface is constructed by a cloth with light-absorbing characteristic.

6. The dark field lighting testing device according to claim 5, wherein the cloth is a black cloth.

* * * * *